(12) United States Patent
Varadan et al.

(10) Patent No.: US 11,819,339 B2
(45) Date of Patent: Nov. 21, 2023

(54) THERMOSENSITIVE NANOSENSOR FOR INSTANTANEOUS TRANSCUTANEOUS BIOLOGICAL MEASUREMENT

(71) Applicant: NANOWEAR INC., Brooklyn, NY (US)

(72) Inventors: Vijay Varadan, State College, PA (US); Pratyush Rai, State College, PA (US); Gyanesh Mathur, State College, PA (US)

(73) Assignee: NANOWEAR INC., Brooklyn, NY (US)

( * ) Notice: Subject to any disclaimer, the term of this patent is extended or adjusted under 35 U.S.C. 154(b) by 514 days.

(21) Appl. No.: 16/916,843

(22) Filed: Jun. 30, 2020

(65) Prior Publication Data

US 2021/0000417 A1    Jan. 7, 2021

Related U.S. Application Data

(60) Provisional application No. 62/869,226, filed on Jul. 1, 2019.

(51) Int. Cl.
| | |
|---|---|
| *A61B 5/01* | (2006.01) |
| *A61B 5/00* | (2006.01) |
| *A61B 5/1486* | (2006.01) |
| *C08L 33/26* | (2006.01) |

(52) U.S. Cl.
CPC .......... *A61B 5/6801* (2013.01); *A61B 5/1486* (2013.01); *C08L 33/26* (2013.01); *A61B 2562/0276* (2013.01); *A61B 2562/0285* (2013.01); *A61B 2562/12* (2013.01)

(58) Field of Classification Search
CPC .......... A61B 5/1486; A61B 2562/0276; A61B 5/6801; C08L 33/26
See application file for complete search history.

(56) References Cited

U.S. PATENT DOCUMENTS

| | | | | |
|---|---|---|---|---|
| 5,622,168 A | * | 4/1997 | Keusch | A61B 5/282 607/152 |
| 2008/0281178 A1 | * | 11/2008 | Chuang | A61B 5/6833 600/347 |
| 2009/0198117 A1 | * | 8/2009 | Cooper | A61B 5/6846 600/347 |
| 2010/0239672 A1 | * | 9/2010 | Kemeny | C08L 51/10 424/78.02 |
| 2011/0003279 A1 | * | 1/2011 | Patel | G01D 7/005 436/1 |
| 2012/0283538 A1 | * | 11/2012 | Rose | A61B 5/14735 600/347 |
| 2016/0361015 A1 | * | 12/2016 | Wang | B32B 27/26 |
| 2017/0188902 A1 | * | 7/2017 | Wang | A61K 31/137 |

* cited by examiner

*Primary Examiner* — Daniel L Cerioni
(74) *Attorney, Agent, or Firm* — Davidson, Davidson & Kappel, LLC

(57) ABSTRACT

A thermosensitive nanosensor includes a substrate having a plurality of vertically standing nanostructures attached thereto, the plurality of vertically standing nanostructure being covered with a conductive material to form conductive coated nanostructures; a thermosensitive hydrogel adjacent to the plurality of conductive coated nanostructures; and a cover layer on top of the thermosensitive hydrogel to prevent loss of moisture and mechanical stress.

31 Claims, 9 Drawing Sheets

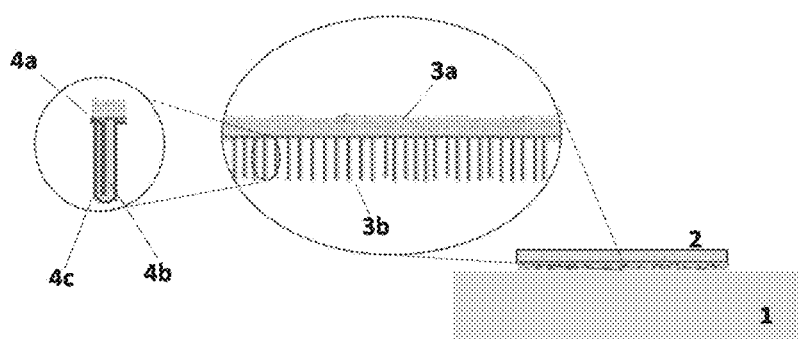
Fig. 1(a)
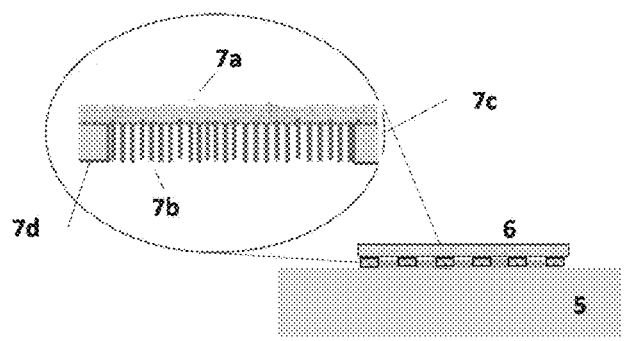 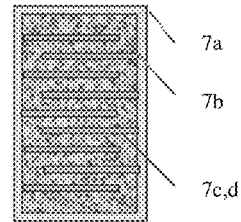
Fig. 1 (b)
Fig. 1(c)

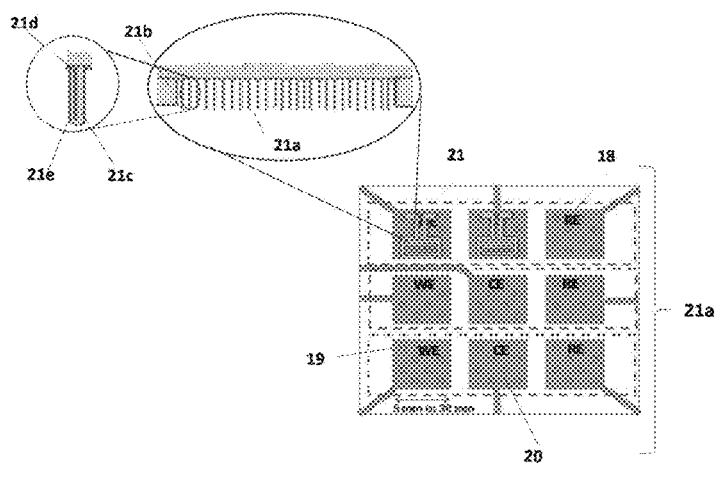
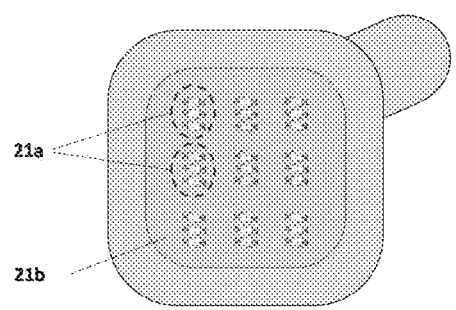
Figure 7(b)                                        Figure 7(a)

THERMOSENSITIVE NANOSENSOR FOR INSTANTANEOUS TRANSCUTANEOUS BIOLOGICAL MEASUREMENT

This application claims priority to U.S. Provisional Application Ser. No. 62/869,226, entitled Thermosensitive Nanosensor For Instantaneous Transcutaneous Biological Measurement, filed Jul. 1, 2019, the entire disclosure of which is hereby incorporated by reference.

FIELD OF THE INVENTION

The present invention relates to the field of sensors for instantaneous transcutaneous biological measurement, in particular nanosensors.

BACKGROUND

The top skin surface stratum corneum is made of dead skin. The moisture level of the layer can vary depending on the sweat secretion, ambient temperature and humidity, rate of transpiration (skin losing moisture) and any topical moisturizer applied to the skin.

When a nanosensor electrode comes in contact with the skin, the transpiration through the skin results in accumulation of moisture at the electrode-skin interface. The electrode-skin interface acts as a moisture barrier. Due to insufficient moisture at the electrode-skin interface, the biopotential signal has high baseline noise. The gradual moisture accumulation at the electrode-skin interface results in the reduction of baseline noise and improvement in biopotential signal quality. The time taken for gradual moisture accumulation is the settling time for the electrode.

The initial skin moisture, the rate of transpiration, skin roughness and skin dryness and very low collagen level in the skin have an effect on settling time. Skin with high moisture content, smoothness, high rate of transpiration and high collagen content results in a shorter settling time. Skin with low moisture, roughness, low rate of transpiration and low collagen level results in a longer settling time.

SUMMARY OF INVENTION

In accordance with an embodiment of the present invention a thermosensitive nanosensor is provided which comprises: a substrate sandwiched between the insulating layer and a conductive layer; vertically standing nanostructures attached to the substrate; a conductive material on top of the nanofiber surface; a thermosensitive hydrogel layer on top of the conductive layer; and a cover layer on top of the thermosensitive hydrogel to prevent loss of moisture and mechanical stress.

In accordance with another embodiment of the present invention, a thermosensitive nanosensor includes a substrate having a plurality of vertically standing nanostructures attached thereto, the plurality of vertically standing nanostructure being covered with a conductive material to form conductive coated nanostructures; a thermosensitive hydrogel adjacent to the plurality of conductive coated nanostructures; and a cover layer on top of the thermosensitive hydrogel to prevent loss of moisture and mechanical stress. The substrate may include a fabric sandwiched between an insulating layer and conductive layer.

In accordance with other aspects of the above embodiments: the cover layer may encase the thermosensitive hydrogel; the cover layer may be provided as coating over the thermosensitive hydrogel; each of the plurality of the conductive coated nanostructures may be coated with the hydrogel, and the hydrogel is coated with the cover layer; the thermosensitive hydrogel may surround the plurality of the conductive coated nanostructures; the thermosensitive hydrogel may be applied as a protective conformal coating film; and/or the thermosensitive hydrogel may be interdispersed among the conductive coated nanostructures. In accordance with further aspects of these embodiments: the thermosensitive hydrogel may include a plurality of hydrogel strips; or the thermosensitive hydrogel and cover layer may form a covered thermosensitive hydrogel ring which surrounds the plurality of the conductive coated nanostructures.

In accordance with other aspects of the above embodiments: the nanostructures may be made of a polymer; the polymer may be embedded into a matrix polymer to form a yarn and the yarn may be a micro denier yarn; the matrix polymer may be made of a material selected from the group consisting of polystyrene, polyvinyl alcohol, ethylene vinyl alcohol, polyacrylamide and poly lactic acid; the matrix polymer may be made of a polyethylene terephthalate modified with sulfonated isocyanate; the nanostructures may be coated with a conductive material; the conductive material may comprise at least one of metals, alloys, and graphene structures; the nanostructures may be made of a polymer material selected from the group of polyesters consisting of polyethylene terephthalate, polyethylene naphthanate or polybutylene terephthalate; the nanostructures may be made of a polyester and/or polyether-based polyurethane; and/or the nanostructures may be made of polyolefins such as polypropylene.

In accordance with other aspects of the above embodiments: hydrogel may be a hydrogel polymer network having hydrophilic groups selected from the group consisting of amines, amides, and acrylates; the hydrogel may be an interpenetrating polymer network gel; the interpenetrating polymer network gel may include polyacrylamide and polyacrylate; the hydrogel may be selectively crosslinked by varying the concentration of initiator used during hydrogel polymerization; the thermosensitive hydrogel may have micelle like structure which opens up on contact with moisture; an enzyme or buffer may be included in the hydrogel, the enzyme or buffer selected to detect a metabolite; the hydrogel may have a comb-like structure formed by grafting polymer chains with hydrophilic end groups such as amines, amides, acrylates; and/or the cover layer may be in the form of elastomers, fibers or films form from at least one of the natural, synthetic, and inorganic polymers.

In accordance with another embodiment of present invention, a method of measuring biopotential signals includes applying the thermosensitive nanosensor according to one of the above embodiments to the skin of a human subject and measuring biopotential signals using the nanosensor.

In accordance with another embodiment of present invention, a method of measuring biopotential signals includes applying the thermosensitive nanosensor according to one of the above embodiments to the skin of a human subject and measuring hemodynamic parameters using the nanosensor.

In accordance with another embodiment of present invention, a method of measuring hemodynamic parameters includes applying the thermosensitive nanosensor according to one of the above embodiments to the skin of a human subject and performing imaging and electro anatomic mapping applications using the thermosensitive nanosensor.

In accordance with another embodiment of present invention, a 3-electrode chemical cell, comprising an array of thermosensitive nanosensors according to one of the above embodiments interconnected to provide a working electrode, a reference electrode and a counter electrode.

BRIEF DESCRIPTION OF THE DRAWINGS

FIG. 1(a)-(c) illustrate nanosensor-hydrogel stacks according to embodiments of the present invention.

FIGS. 7(a) and 7(b) show a sensor with a sensor array with working electrode (WE), counter electrode (CE) and reference electrode (RE) set shown, where interdigitated electrodes may be used for skin oil content and hydration.

DETAILED DESCRIPTION

Figure 2:
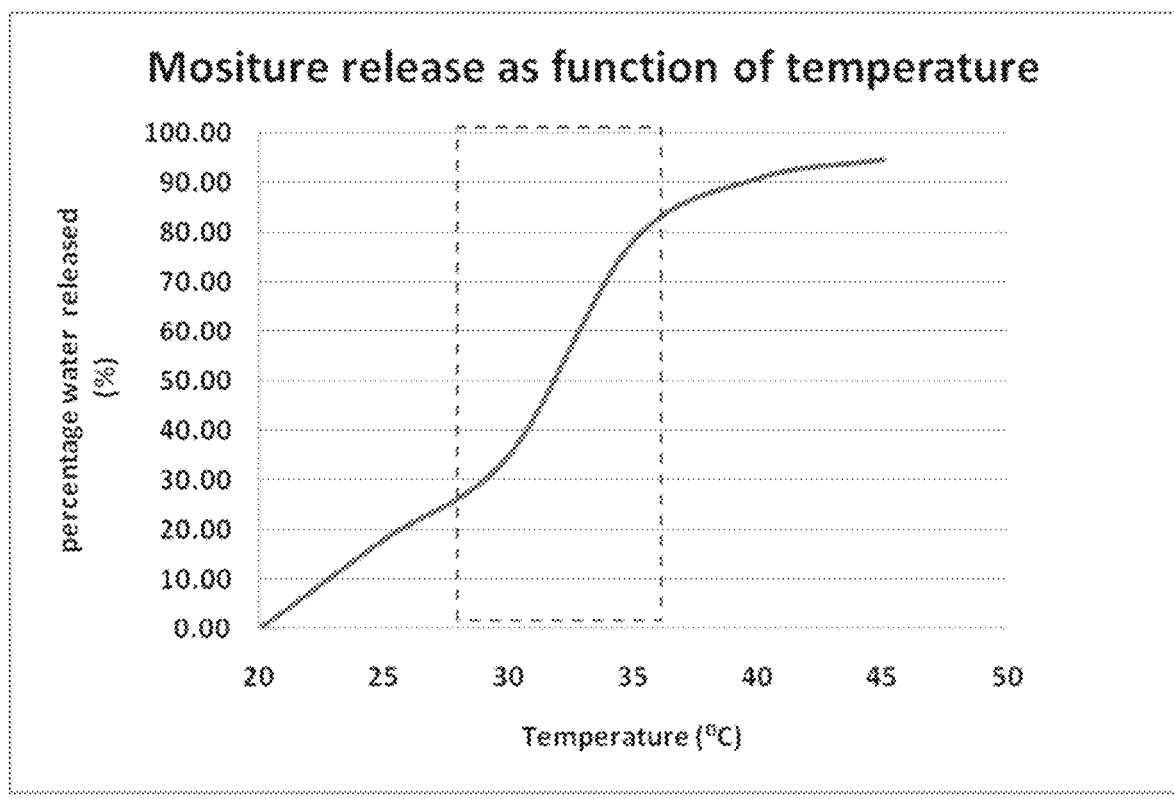
FIG. 2 shows moisture release from the hydrogel as a function of temperature

A hydrogel conformal film on top of the nanosensor surface or a hydrogel film staked with the nanosensor can provide moisture for the skin to make it moist for better nanosensor-skin contact. This results in a short settling time or negate the settling time for subjects with varying skin characteristics. The hydrogel only acts as a source of moisture but the electrode is still a dry electrode. The electrical interface with the skin is still formed by the nanostructures, unlike the gel-based electrodes that rely on the wet chemistry of the salts in the gel to make the electrical interface with the skin.

In accordance with various embodiments of the present invention a wearable nanosensor hydrogel stack is provided. The stack may be comprised of a cloth-based nanosensor with vertically standing polymer nanofibers coated with electrically conductive material to form a conductive nanostructured surface in a predefined pattern. This nanostructured surface also has a film of hydrogel that responds to change in ambient temperature and release moisture. The hydrogel film is placed on top of the nanostructured surface as a conformal coating or placed in form of a pattern that interpenetrates with the pattern of the nanostructured surface. The hydrogel film has a cover layer on top of it to prevent moisture loss and mechanical stress during wear.

This hydrogel-nanosensor stack forms a good nanosensor-skin contact by introduction of moisture at the nanosensor-skin interface, which is triggered immediately after the stack comes in contact with skin and detects skin temperature. The stack retains moisture at room temperature and can be recharged when it comes in contact with a moisture source. The stack forms a good nanosensor-skin contact and instantaneously picks up transcutaneous biological measurements. It can be used for applications that involve capturing biopotential signals, electroactive imaging/mapping application, detection of electrical signal originating from implantable medical devices, probes and catheters, detection of skin metabolites, skin hydration, oil content and drug delivery through the skin.

FIGS. 1(a) through 1(c) illustrate wearable nanosensor hydrogel stacks in accordance with the present invention. In both FIG. 1(a) and FIG. 1(b), the stack (2, 6) comprises of cloth-based nanosensor with vertically standing polymer nanofibers coated with electrically conductive material to form a conductive nanostructured surface (3b, 7b) on a cloth substrate (3a, 7a). The nanostructured surface (3b, 7b) also has a film of hydrogel that responds to skin (1,5) temperature and release moisture.

In the nanosensor hydrogel stack (2) of FIG. 1(a), a hydrogel film (4b) is placed on top of the nanostructures (4a) of the nanostructured surface (3b) as a conformal coating. In the nanosensor hydrogel stack (6) of FIG. 1(b), the hydrogel is in the form of a hydrogel pattern (7c) that interpenetrates or is interdispersed with the pattern of the nanostructured surface (7b) as illustrated in FIG. 1(c). In both the stack (2) and the stack (6), the hydrogel film (4b, 7c) has a cover layer (4c, 7d) on top of it to prevent moisture loss and mechanical stress during wear. The cover layer (4c, 7d) is made of interwoven fibers or non-woven thin film of synthetic polymers such as polyester, butyl rubber, polyolefins etc.

This hydrogel-nanosensor stack forms a good nanosensor-skin contact by introduction of moisture at the nanosensor-skin interface, which is triggered immediately after the stack comes in contact with skin and detects skin temperature. The stack retains moisture at room temperature and can be recharged when it comes in contact with a moisture source.

Thermosensitive Hydrogels Formulation:

Several gels have the characteristic of undergoing a discontinuous volume change upon changes in temperature and are classified as Thermosensitive Hydrogels. This phenomenon is due to the phase transition in the hydrogel at the designated temperature, and at this phase transition temperature (PTT) the swelling ratio of the hydrogel undergoes a sudden change.

There are various hydrogels which exhibit the thermosensitive behavior, however, in accordance with various embodiments of the present invention, hydrogels having a phase transition temperature ranging between 17 to 60° C. are used. In particular, acrylamides and substituted acrylamides show a clearly defined phase transition temperature ranging between 17 to 60° C. In particular, N-isopropyl acrylamide (NIPA, $C_6H_{11}NO$) copolymerized with N,N' methylene bis acrylamide (BIS, $C_7H_{10}N_2O_2$) gives the phase transition temperature of 33° C. which is useful for skin contact application.

Hydrogels can be cationic, anionic or neutral in nature and their hydrophilicity is due to the presence of $-NH_2$, $-COOH$, $-OH$, $-CONH_2$ groups which leads to their swelling in the presence of water.

Hydrogel Synthesis and Characteristics:

Exemplary, hydrogels were synthesized based on N, isopropyl acrylamide (NIPA) as their phase transition temperature was in the range of 33-37° C. N,N' methylene bis acrylamide ($C_7H_{10}N_2O_2$) (BIS) was used as a crosslinking agent. Ammonium per sulfate (APS) was used as a Redox initiator and Sodium meta bi sulfite (SMBS) as an accelerator. All reactants were dissolved in deionized water and the reaction was carried out under Nitrogen blanket at 5° C. for 12 hrs.

$$-(C_6H_{11}NO)-_{X1}+-(C_7H_{10}N_2O_2)-_{X2} \xrightarrow{APS,SMBS} \text{NIPA Hydrogel} \qquad (Eq. 1)$$

The NIPA-BIS hydrogel (Eq. 1) can be prepared in deionized water by adding 6 to 8 weight % NIPA and 1 to 2 weight % BIS then purging with Nitrogen. After this a mix of 2 to 4 weight % Ammonium per sulfate (initiator) and Sodium Meta BiSulfite (accelerator) in deionized water was added to the above prepared solution and the solution was again purged with Nitrogen. The solution was kept in an airtight container at 5° C. for 12 hours. After completion of the reaction, the solution was heated to 60° C. when the NIPA-BIS hydrogel separated from the solution due to phase transition. The NIPA-BIS hydrogel was then washed and dried for further evaluation of its swelling and phase transition characteristics as a function of temperature as shown in FIG. 2.

The NIPA-BIS hydrogel formulations can be classified based on their degree of crosslinking as low, medium and high. The degree of crosslinking is adjusted by varying the percentages of redox initiator and accelerator in the solution. Performance of the nanosensor-hydrogel stack of hydrogels with different degrees of crosslinking is shown in the table below. All the stacks show less than 5 seconds of time taken to obtain ECG signal after the nanosensor-hydrogel stack comes in contact with the skin. Accordingly, the optimal degree of crosslinking is determined by other characteristics such as film tackiness, film thickness after swelling (Tables 1 and 2).

TABLE 1

Thermosensitive hydrogel formulations with varying degree of cross linking

| Formulation | III | IV | V |
| --- | --- | --- | --- |
| Gel cross linking | Low | Medium | High |
| Skin moisture (Dryness; oiliness; roughness) | −2; 0; −2 | 0; 1; 0 | 0; 1; 0 |
| Particle size (after manual grinding) | Medium size | Very fine | Granular |
| Water addition (3 sprays) | Swell very fast | Water diffuses through fine powder | Takes time in wetting and swelling |
| Film formation | Forms continuous gel | Forms continuous gel | Form continuous gel |
| Film Tackiness | Slightly sticky | Slightly sticky | Very sticky |
| Film thickness | Medium thickness | Medium thickness | High thickness |
| Signal Acquisition (1 and 2 horizontal) | Instantaneous | Instantaneous | Instantaneous |
| Signal Acquisition (1 and 3 vertical) | Instantaneous | Instantaneous | Instantaneous |

TABLE 2

Formulation details for low, medium, high cross-linked hydrogels of Table 1

| Formulation | III | IV | V |
| --- | --- | --- | --- |
| Gel cross-linking | LOW (wt %) | MEDIUM (wt %) | HIGH (wt %) |
| 1-N-Isopropyl Acrylamide | 6 | 8 | 8 |
| 2-N,N' Methylene bis Acrylamide | 0.06 | 0.08 | 0.08 |
| 3-Ammonium per Sulfate | 0.12 | 0.16 | 0.32 |
| 4-Sodium Meta BiSulfite | 0.015 | 0.025 | 0.05 |

Note:
All these percentages are with reference to the weight of water.

Nano/Micro Sensor Fabrication:

The nanosensor fabrication may involve steps of embedding polymer nanofibers into a matrix polymer to form a yarn; dissolving the matrix polymer to expose the polymer nanofibers; and coating the polymer nanofibers in a film. The yarn can be a micro denier yarn. The micro denier yarn can have a helical structure. The method can further include a step of imparting an electrostatic charge to the yarn prior to dissolving the matrix polymer. The polymer nanofibers can be made of a polymer material selected from the group consisting of polyethylene terephthalate, polyethylene naphthalate or polybutylene terephthalate. The polymer nanofibers can be made of a polyester. The polymer nanofibers can be made of a polyurethane. The matrix polymer can be made of a material selected from the group consisting of polystyrene, polyvinyl alcohol, ethylene vinyl alcohol, polyacrylamide or poly lactic acid. The matrix polymer can be made of a polyethylene terephthalate modified with sulfonated isocyanate. The film can be a conductive material selected from the group consisting of silver, gold, platinum, polyaniline, polypyrole, poly(3,4-ethylenedioxythiophene). The film can be a metal oxide film. The film can be a piezoelectric material film.

Figure 3:
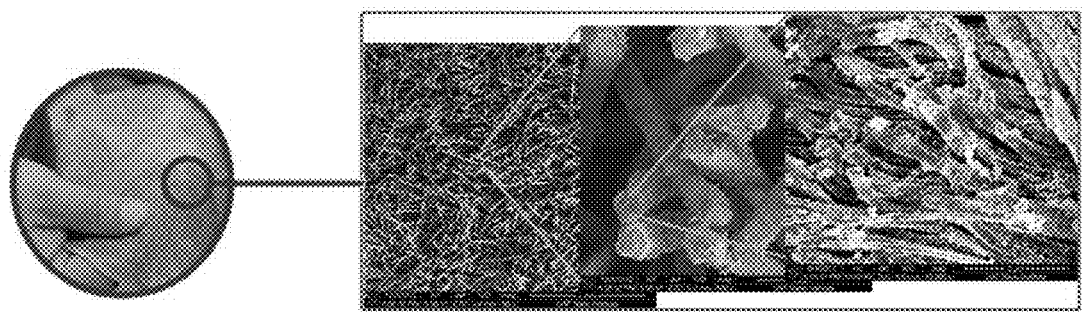
FIG. 3 shows cloth based nanosensors with vertically standing nanostructures.

A method for manufacturing of hybrid nanostructured textile sensors (FIG. 3) comprises: feeding one or more polymers and a matrix polymer in molten form through respective extruders to a spinneret to produce fibers having filaments of the one or more polymers in the matrix polymer, the filaments having dimensions of from about 10 to about 100 nanometers; cutting the fibers to a length of from about 0.1 to about 1.5 mm to produce nanofibers; activating the cut nanofibers in a reactor; drying the activated nanofibers; applying an adhesive to a conductive fabric; depositing the activated nanofibers as vertically standing nanofibers, the depositing step including performing an electrostatic and/or pneumatic assisted deposition process using a high strength electrostatic field of 2 kV/cm-10 kV/cm to electrostatically charge the activated nanofibers and deposit the electrostatically charged activated nanofibers as vertically standing nanofibers; curing the conductive fabric containing the vertically standing nanofibers; and electroless plating the vertically standing nanofibers, the electroless plating including dissolving the matrix polymer on the nanofiber surface to expose embedded nanostructures on the filaments, coating the nanofiber surface with a conductive material, and drying the conductive material to form a conductive film on the nanofibers, and annealing the conductive film coated nanofibers.

In a different variation of this method, a single component micro denier yarn of 10-20 μm diameter is used for making microsensors. The method includes cutting of fibers to a length of from about 0.1 to about 1.5 mm; activating the cut microfibers in a reactor; drying the activated microfibers; applying an adhesive to a conductive fabric; depositing the activated microfibers as vertically standing nanofibers, the depositing step including performing an electrostatic and/or pneumatic assisted deposition process using a high strength electrostatic field of 2 kV/cm-10 kV/cm to electrostatically charge the activated microfibers and deposit the electrostatically charged activated microfibers as vertically standing nanofibers; curing the conductive fabric containing the vertically standing microfibers; and electroless plating the vertically standing microfibers, the electroless plating including coating the microfiber surface with a conductive material, and drying the conductive material to form a conductive film on the microfibers, and annealing the conductive film coated microfibers.

A more detailed description of these processes can be found in U.S. Pat. No. 10,131,993 B2 "Large Scale Manufacturing of Hybrid Nanostructured Textile Sensors," and U.S. Pat. No. 10,231,623 B2 "Roll-to-roll Printing Process for Manufacturing a Wireless Nanosensor," the entire disclosures of which are hereby incorporated by reference.

Wearable Hydrogel-Nanosensor Stack:

The application of the NIPA-BIS hydrogel on nanosensor surface can be done by either spray coating the gel on the vertically standing nanofibers attached to the sensor surface or by providing a ring of hydrogel around the periphery of the sensor.

Application of Hydrogel as Annular Ring:

In some embodiments, the hydrogel can be applied as an annular ring. In the application of hydrogel as an annular ring around the sensor, the gel requires structural integrity for continuous skin contact as well as consequent wear on and removal by the wearer of the garment with the sensor-hydrogel stack. To provide such structural integrity, the hydrogel can be embedded in an annular ring structure made of open cell foam made of materials such as polyurethane to make a hydrogel matrix. This matrix can then be applied as annular ring around the sensor. An exemplary formulation of NIPA-BIS hydrogel that can be embedded in the open cell foam is—deionized water—60 ml, NIPA—4.8 grams, BIS—2.5 wt % of NIPA, APS—4 wt % of NIPA, SMBS—15.6% of APS. The hydrogel strips 7c of FIGS. 1(b) and (c) can be made in the same manner.

Figure 4A:
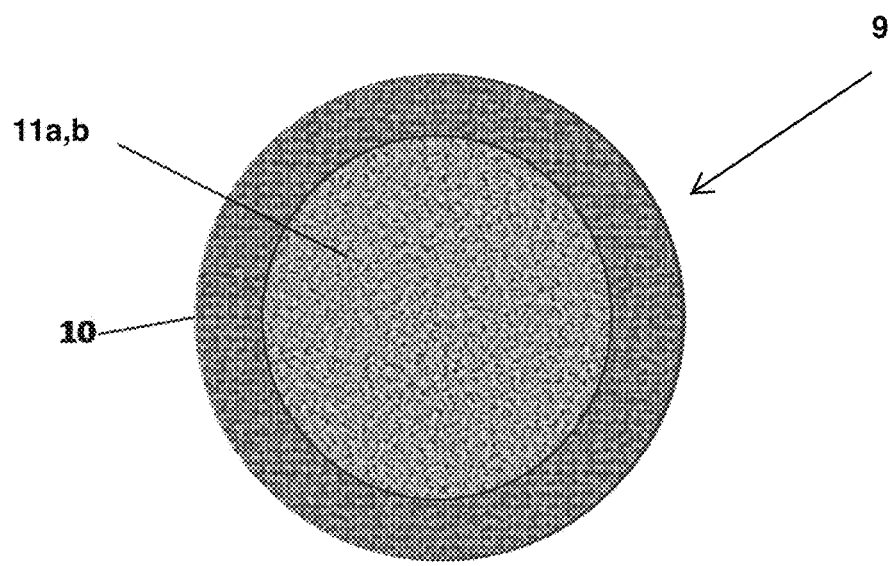
FIGS. 4(a) and 4(b) show a nanosensor-hydrogel stacks according to another embodiment of the present invention.
Figure 4B:
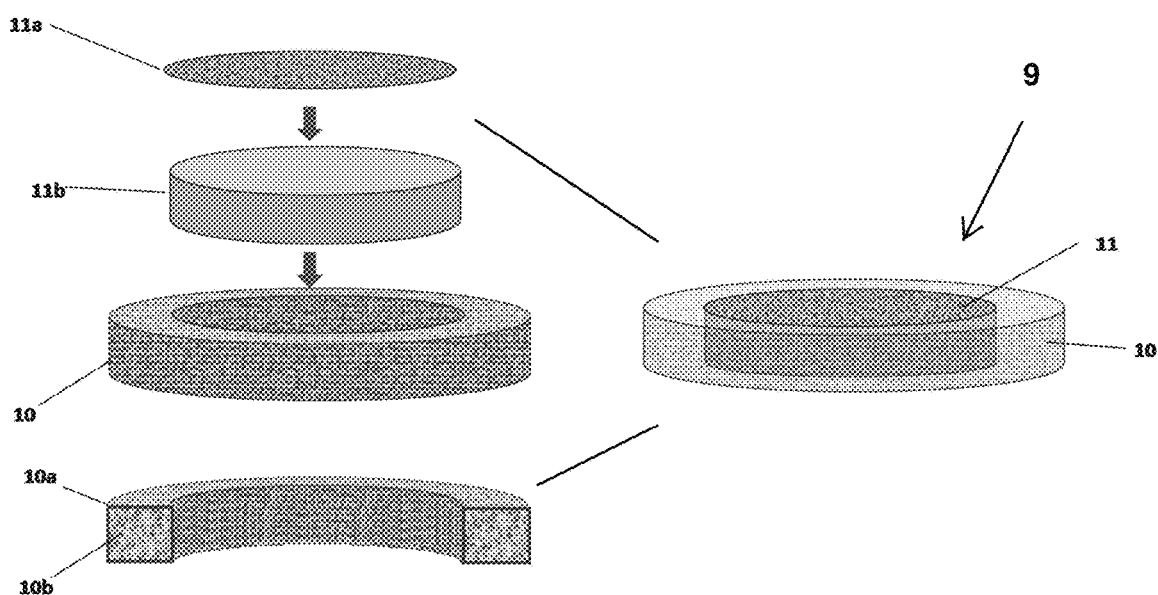

The hydrogel matrix was made into a cylindrical ring as shown in FIG. 4(a,b). FIG. 4a shows a puck shaped nanosensor assembly 9 including fabric covered hydrogel ring 10. FIG. 4b shows the fabric covered hydrogel ring 10 where the hydrogel is embedded in open-cell foam 10b that is in the shape of the ring where inner diameter is equal to the diameter of the nanosensor 11a. The hydrogel—open cell foam structure 10b of ring 10 is covered with a layer of fabric 10a. The puck-shaped nanosensor assembly 9 in FIG. 4a is explained further in FIG. 4b. The nanosensor disc 11a is placed on top of a backing material 11b of a certain height. The backing material height is equal to the hydrogel—open cell foam—fabric structure height. The backing material 11b can be cushioning material such as neoprene foam, silicone rubber foam. The covering fabric 10a can be coarse weave fabric material such as polyester, nylon. The nanosensor disc 11a is both the substrate (e.g. 3a, 7a in FIGS. 1(a), 1(b)) and the nanofibers (e.g. 3b, 7b in FIGS. 1(a),(b)). The fabric covered ring 10 also provides a cloth-like feel in the hydrogel regions when the wearer puts it on. This hydrogel-nanosensor stack can be integrated into a wearable from factor.

Application by Spray Coating:

Two different processes can be used to spray coat the NIPA based hydrogel over the conductive coated nanostructures 4a of FIG. 1(a).

In the first process, the reactants are dissolved in deionized water and the solution is stored under nitrogen. The reaction is allowed to proceed for approximately 9-12 hours. When the viscosity of the solution starts to build up, the solution is transferred to a reservoir connected to a spray gun. The spray gun is used to apply a conformal coat of the solution on the vertically standing nanostructures of the nanosensor by using pressurized nitrogen gas. The size and rate of droplets can be controlled by the flow rate of nitrogen gas. The solution's low viscosity is because the polymerization is partially completed. The solution coated on the surface of the nanosensor is allowed to sit for another 3 hours under nitrogen for complete polymerization of NIPA hydrogel.

In particular, the NIPA-BIS hydrogel (Eq. 1) can be prepared in deionized water by adding 6 to 8 weight % NIPA and 0.05 to 0.1 weight % BIS then purging with Nitrogen. After this a mix of 0.1 to 0.4 weight % Ammonium per sulfate (initiator) and 0.01 to 0.5 weight % Sodium Meta BiSulfite (accelerator) in deionized water was added to the above prepared solution and the solution was again purged with Nitrogen. The solution was kept in an airtight container at 5° C. for 12 hours. After completion of the reaction, the solution was heated to 60° C. when the NIPA-BIS hydrogel separated from the solution due to phase transition. The separated NIPA-BIS hydrogel is rehydrated and the gel is transferred to the spray gun.

In the second process, the hydrogel is spray coated after the polymerization step by shear thinning. In this process, during the polymerization process described above in the preceding two paragraphs, laponite/sheet like silica nanoparticles are added (2-5% by weight) or the length of the cross linking polymer chains of the hydrogel are increased by adding more monomers units. This increases the viscoelasticity of the hydrogel. Shear thinning is done by forcing the hydrogel from an antechamber through a 1-3 mm wide slit opening in to the cup of the spray head. This is done at the rate of 1000-1500 mg per sec. Once the shear thinned hydrogel reaches the cup, a torroidal flow of nitrogen in the spray head is used to spray the hydrogel out onto the nanosensor surface. During the shear thinning step the cross linking in the hydrogel is disrupted by shear force due to additives such as laponite. The shear thinning process distorts the cross-linking network to reduce the viscosity of polymerized hydrogel. After the hydrogel is spray coated, it is allowed to restore/recover the broken covalent bonds. The restoration/recovery time for the hydrogel and the amount of shear stress to be applied is dependent on the cross linking density and the length of the inter chain linkages from the hydrogel network. In case of laponite assisted shear thinning step, it is also dependent on the percentage of laponite silica nanoparticles added to the hydrogel that has a direct effect on the extent of cross linking disruption during the shear thinning step.

Washability:

The hydrogel, in the hydrogel-nanosensor stack, can be made washable by coating the hydrogel with a thin elastomeric material such as butyl rubber, polyurethane, silicone elastomer. The elastomeric material film acts as a low elastic modulus semi-permeable barrier that protects the hydrogel from mechanical impact of washing while allowing for moisture to move to and from the hydrogel. The film can be applied by dip coating or spray coating of polymerization solution. The polymerization is done at room temperature or at temperature that is below the phase transition temperature of the hydrogel.

Moisture Recharge of Hydrogel:

During the deswelling process of the hydrogel due to thermal stimuli, for example, skin temperature, the interstitial structure of hydrogel collapses. This starts at the surface of the hydrogel film and this forms a dense layer on the surface of the hydrogel. This layer obstructs the movement of moisture from and to the hydrogel matrix. It is important for the moisture recharge of hydrogel that the movement of moisture to the hydrogel for rehydration is not obstructed.

This obstruction can be rectified and fast rehydration (swelling) response can be achieved by:

1. Controlling the 3D crosslinking of the hydrogel by selective crosslinking at the controlled sites and introducing vinyl groups to create larger interstitial gaps that do not collapse completely upon moisture release. The uncollapsed gaps act as the space for moisture retention during faster rehydration in absence of any molecular bonding. Selective crosslinking can be achieved by varying the concentration of initiator used during hydrogel polymerization.
2. The molecular structure of the hydrogel is modified to have a comb like structure by first having linear poly n-isopropyl acrylamide of various lengths by chain transfer agents and amino end groups which is converted to acrylate end groups and semitelechelic linear chains having various vinyl monomers are grafted to the hydrogel network having one freely mobile side end, thus giving a comb like structure enhancing the hydration rate.
3. To have a micelle like structure which opens up on contact with moisture by having active charge on the pendant site. The micelle like structure also prevents the hydrogel interstitial structure from collapsing due to repellency of the charged groups during the deswelling process.
4. To have an interpenetrating polymer network such as that of polyacrylamide and polyacrylate. This is achieved by having both monomers (for example, NIPA and Acrylic Acid) polymerize with their own monomers or co-monomers without interacting with the other monomer or comonomer to generate an IPN. This prevents the hydrogel interstitial structure from collapsing during the deswelling process.
5. Introduction of hydrophilic groups such as amines, amides, acrylates in the hydrogel polymer network through radical polymerization to be bound as side chains to increase the hydration rate.

Measurement of ECG:

A nanosensor wearable form factor includes completed nanosensor system integration and/or fabrication of the form factor of wearable devices. The processes include cutting, sewing, lamination and/or fusing with another fabric or functional film(s).

Figures 5A, 5B:
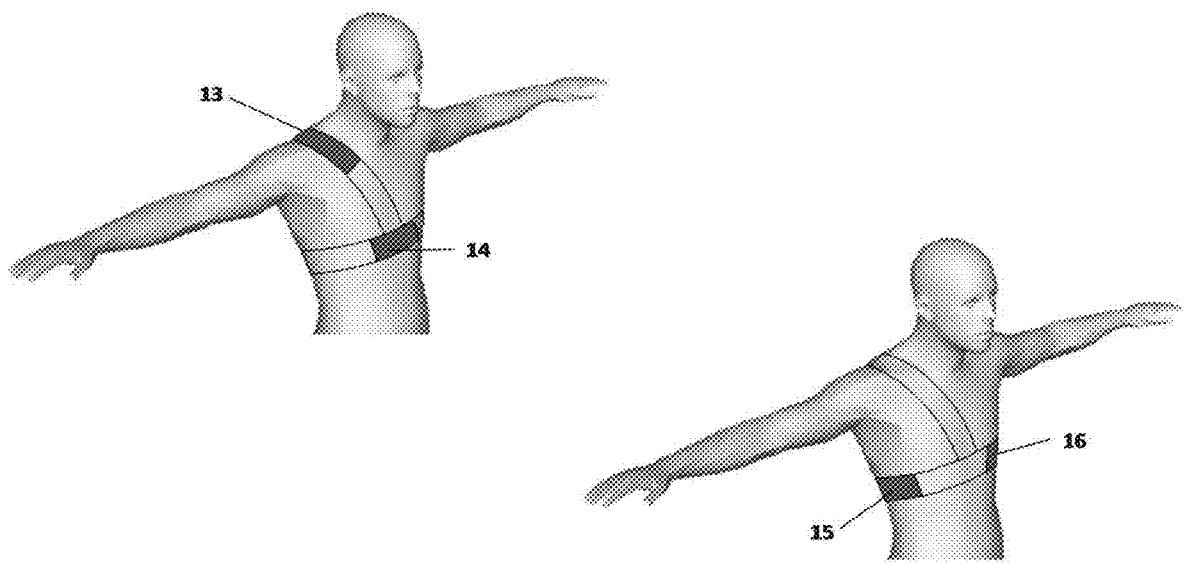
FIGS. 5(a) and 5(b) show a wearable form factor with embedded nanosensors.

An example of a nanosensor wearable form factor for measurement of ECG is shown FIG. 5. The form factor comprises of the vertical band 13 over the right shoulder blade and a horizontal band 14 at the level of the Xyphoid process. The nanosensors can be placed on positions on the opposite sides of the general heart position such as right side 15 and left side 16 of the horizontal band. Position on the vertical band can also be used. An exemplary arrangement of the two bands can also be found in U.S. patent application Ser. No. 15/967,792, filed May 1, 2018, entitled WEARABLE CONGESTIVE HEART FAILURE MANAGEMENT SYSTEM, the entire disclosure of which is hereby incorporated by reference. The nanosensors may, for example, be fabricated as shown in FIGS. 1(a-c) and FIG. 4.

Figure 6:
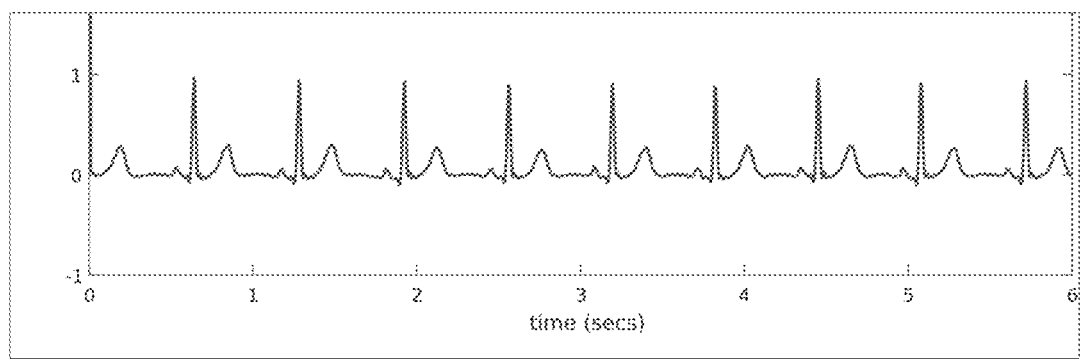
FIG. 6 shows an exemplary ECG histogram acquired by nanosensor-hydrogel stack.

During extended periods of time, the nanosensor-hydrogel stack shows less than 5 seconds of settling time (thus providing an instantaneous response) for the ECG signal. A sample ECG strip is shown in FIG. 6.

The Extended ECG wear test shows instantaneous ECG signal acquisition even after 6 days of wear on wear off testing. The test summary is shown in Table 3.

TABLE 3

Testing of Hydrogel Nanosensor stack for extended wear test for ECG measurement

| S. No. | Time since sensor Fabrication | Skin Moisture (moist, oily, rough) * | | Test Duration | Signal Acquisition |
|---|---|---|---|---|---|
| | | Front left sensor location | Front right sensor location | | |
| 1 | 6 hrs | 0, 1, 0 | 0, 1, 0 | 30 min | ECG signal was acquired instantly |
| 2 | 7 hrs 10 min | 0, 4, 0 | 1, 4, 1 | 30 min | ECG signal was acquired instantly |
| 3 | 96 hrs | 0, 1, 0 | 0, 1, 0 | 30 min | ECG signal was acquired instantly |
| 4 | 100 hrs 30 min | 0, 4, 0 | 0, 4, 0 | 120 min | ECG signal was acquired instantly |
| 5 | 120 hrs 20 min | 0, 4, 0 | 0, 4, 0 | 30 min | ECG signal was acquired instantly |
| 6 | 126 hrs 35 min | 2, 5, 4 | 2, 5, 4 | 60 min | ECG signal was acquired instantly | moisture meter shows skin moisture, oil and roughness levels on an arbitrary scale of −5 to 5

In the test of Table 3, continuous ECG signal is obtained for the duration of the wear and during movements such as walk slowly, brisk walking. The test was conducted using the form factor of FIG. 5 and the hydrogel nanosensor stack of FIG. 4.

Catheter Location Detection Application in Electroactive Mapping:

The inventive hydrogel-nanosensor stacks described herein can be used for catheter location detection in catheter ablation procedures and 3D mapping of the heart. It uses high frequency electric pulses that originate from the catheter and are detected by reference patches placed at multiple locations on skin at front and back of patient's body. Using the hydrogel-nanosensor stacks in accordance with the present invention, with their low skin-electrode impedance without skin preparation, as the reference patches can reduce the preparation time during the procedure and provide same level of performance with smaller electrode size as compared to the conventional electrode. This is beneficial for patients with small body size and leaves more space for 12 lead ECG electrodes and defibrillation patches.

Skin Metabolite Detection:

The inventive hydrogel-nanosensor stacks described herein can be used for detection of metabolites in the skin tissue when in contact with the skin.

FIG. 7(a) show a patch containing an array of nine electrochemical cells 21a surrounded by a thermo responsive hydrogel 21b, providing a hydrogel nanosensor stack in accordance with an embodiment of the invention. These multiple sensor arrays 21a are spread around to cover a surface area that can be the wearer's skin or open wound where the patch can be used as a wound dressing. As with the hydrogel nanosensor stacks of FIGS. 1(a-c) and 4, a cover layer maybe provided over the hydrogel 21b in the same manner discussed above with regard to FIGS. 1(b-c) and 4. FIG. 7(b) shows the electrochemical cell 21a in further detail.

Referring to FIG. 7(b), each electrochemical cell 21 includes three reference electrodes 18, two counter electrodes 20, two working electrodes 19, and two inter-digitated (IDT) nanostructured electrodes 21. Within each electrochemical cell 21a, the working electrode (WE) 19 and counter electrode (CE) 20 are nanostructured electrodes in the form of hydrogel-nanosensor stacks. The reference electrode (RE) 18 is a silver-silver chloride printed electrode and is also covered with hydrogel. A working electrode, a counter electrode and a reference electrode form a 3-electrode electrochemical cell. While all three electrodes are covered with hydrogel, only the working electrode has a hydrogel-enzyme/buffer formulation The hydrogel-enzyme/buffer formulation is preferably one of the polymerization mixes described in TABLE 2, except that the weight percentages will be based on the weight of the buffer solution instead of water. The quantity of enzyme mixed in is based on the enzyme activity required for sensor application. The enzyme/buffer chosen will vary depending on the application, and examples are provided below with respect to detection of skin PH, skin hydration, and Hyaluronic Acid. The dispersion of the mix is important to prevent agglomeration and achieve homogenous polymerization mix. Skin hydration can be detected by change in skin conductivity or impedance.

Skin impedance can be measured by the two inter-digitated (IDT) nanostructured electrodes 21, which form a interdigitated electrode pair. In this regard, inter-digitated electrodes are a pair of comb-like electrodes that are interlocked and form a narrow channel in between the electrodes. The electrodes 21a and the channel 21b are covered with hydrogel film as shown in FIG. 7. The hydrogel film 21c is placed on top of the nanostructures 21d of the nanostructured surface 21a as a conformal coating. The hydrogel also fills the channel 21b. The hydrogel film (21c, 21b) has a cover layer 21e on top of it to prevent moisture loss and mechanical stress during wear. The inter-digitated electrode pairs are used for skin impedance, metabolite detection and skin hydration measurement in different configurations. The configurations can be 2 electrodes configuration for skin hydration, 3/4 electrodes configuration for bio-impedance by measuring impedance across a frequency spectrum and metabolite detection by measuring action potential. Impedance can be electrically modeled as a circuit that provides an equivalent impedance to skin (see, for example, FIG. 8).

Functionalization of hydrogel on nanosensors can be done by covalent cross linking between the acryl amide of the hydrogel matrix and the metabolite specific enzyme. Multiple working electrodes with different enzymes that target specific metabolites can be placed together to form a nanosensor array.

The following metabolites can be detected by the hydrogel-nanosensor stack while in contact with the skin:

(1) Hyaluronic Acid (HA): Skin has 50% of body's total HA level. HA is essential for skin tissue hydration, which effects over all skin tone. HA can be detected by hydrogel-nanosensor stack with Hyaluronidases immobilized in the hydrogel matrix. The enzyme hyaluronidase immobilized in the hydrogel, saturated with a buffer with pH of 4.5-6, when released in the skin interact with the HA in the skin to hydrolyze the HA. The hydrolysis results in a change in potential measured across an electrochemical cell shown in FIG. 7(b).

(2) pH of Skin: The pH is due to skin's acid mantel. It acts as a barrier to bacteria, viruses and other contaminants. The average value of skin pH is 4.2 to 5.6 in absence of excess sweat secretion or oil secretion. Skin with pH values below 5.0 are healthier, more hydrated, and have a stronger barrier function than those above 5.0. The change in pH can be detected by hydrogel-nanosensor stack with buffer solution loaded hydrogel. For example, the hydrogel may be saturated with potassium chloride electrolyte. The electrode pair can be made of two nanosensor-hydrogel stacks, made for example in accordance with FIG. 1a. One of the electrodes has an impermeable hydrogel (phase transition temperature higher than body temperature), while the other electrode has a phase transition temperature close to body temperature and is permeable to skin secretion. The electrode and electrolyte with permeable hydrogel interacts with skin secretion. The potential difference across these electrodes is indicative of pH level in the skin secretions. See FIG. 7.

Figure 8:
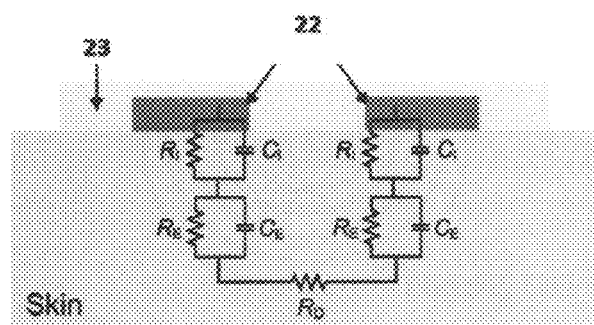
FIG. 8 shows a schematic depiction of nanosensor-hydrogel based electrochemical cell for monitoring skin condition.

(3) Skin hydration: Skin hydration gets affected by loss of HA from the skin, skin pH, skin oil. Well hydrated skin has better complexion and elasticity. Skin hydration can be detected by change in skin conductivity or impedance. Skin impedance measured by the two inter-digitated (IDT) nanostructured electrodes 22 with a hydrogel coating 23 (FIG. 8). Impedance can be electrically modeled using an equivalent circuit. The $R_I$ and $C_I$ denote contact interface between the electrode and the skin surface. The epidermis is modeled $C_E$ and $R_E$. The dermis and underlying subcutaneous tissues are denoted by $R_D$. The $R_I$ and $C_I$ are dependent on applied pressure and the moisture content of the skin. The hydrogel-nanosensor stack (IDT electrodes 22 and hydrogel 23) forms a homogenized interface between the nanosensor and the skin surface so that the changes in impedance characteristics due to hydration of the subcutaneous skin can be captured. The hydrogel-nanosensor stack can be of the construction shown, for example, in FIG. 1a, 1(b,), or 7.

Figure 9:
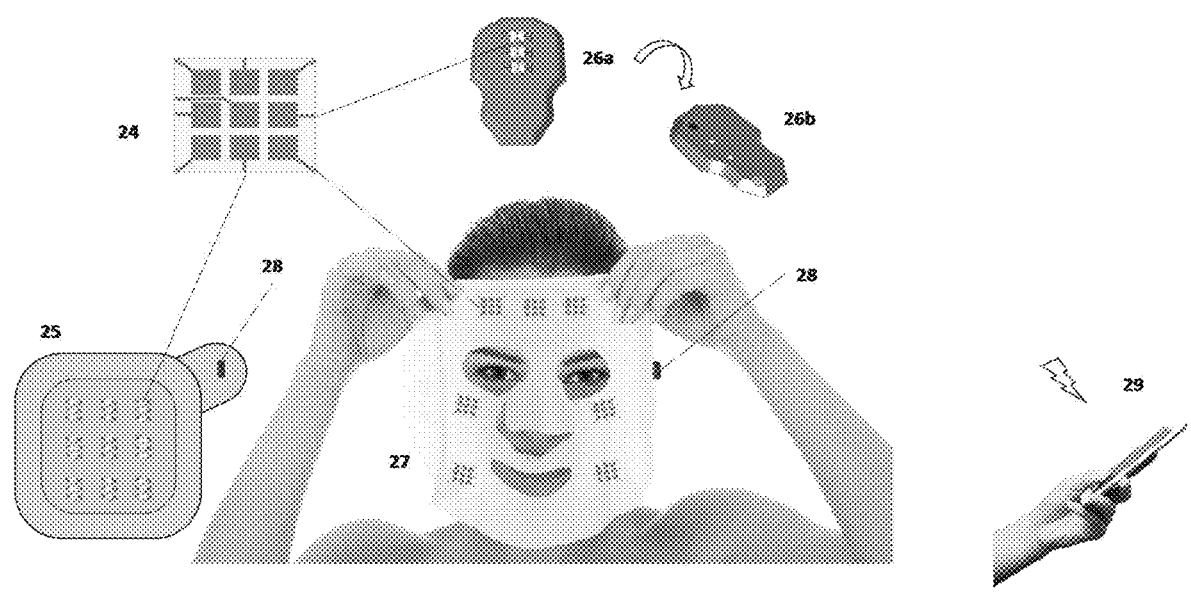
FIG. 9 shows nanosensor arrays on a patch, a wearable mask, and a handheld sensor, in communication with a smart phone.

The electrochemical cell made of hydrogel-nanosensor stacks such as those discussed above for detection of skin PH, skin hydration, and Hyaluronic Acid, can be integrated in a film made of materials such as silicone, polyurethane, collagen to form a wearable measurement platform. Referring to FIG. 9, an array of such electrochemical cells, each of them with a specific hydrogel-enzyme/buffer stack 24, can be integrated into a film to make a patch 25, handheld probe 26a,b or a wearable mask or a band 27. The hydrogel enzyme buffer film (21c, 21b) forms a coat on nanosensor structure as well as the spacing in between as shown in FIG. 7. The hydrogel film (21c, 21b) has a cover layer 21e on top of it to prevent moisture loss and mechanical stress during wear. The wearable film can be used for monitoring skin condition health and correlate the skin health status with the skin care products being used. An electrical module 28 can be attached to this array of such electrochemical cells, which may for example, include circuity such as potentiostats connected to each cell for signal measurement and electronics for capturing the signals and transmitting them to a handheld wireless communication device 29.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

Obvious variants of the disclosed embodiments are within the scope of the description and the claims that follow.

All references cited herein, as well as text appearing in the figures and tables, are hereby incorporated by reference in their entirety for all purposes to the same extent as if each were so individually denoted.

What is claimed is:
1. A thermosensitive nanosensor comprising:
a substrate comprising a plurality of vertically standing nanostructures attached thereto, the plurality of verti- cally standing nanostructure being covered with a conductive material to form conductive coated nanostructures;
a thermosensitive hydrogel adjacent to the plurality of conductive coated nanostructures;
a cover layer on top of the thermosensitive hydrogel to prevent loss of moisture and mechanical stress.

2. The thermosensitive nanosensor of claim 1, wherein the substrate includes a fabric sandwiched between an insulating layer and conductive layer.

3. The thermosensitive nanosensor of claim 1, wherein the cover layer encases the thermosensitive hydrogel.

4. The thermosensitive nanosensor of claim 1, wherein the cover layer is provided as a coating over the thermosensitive hydrogel.

5. The thermosensitive nanosensor of claim 1, wherein each of the plurality of the conductive coated nanostructures are coated with the hydrogel, and the hydrogel is coated with the cover layer.

6. The thermosensitive nanosensor of claim 1, wherein the thermosensitive hydrogel is interdispersed among the conductive coated nanostructures.

7. The thermosensitive nanosensor of claim 6, wherein the thermosensitive hydrogel includes a plurality of hydrogel strips.

8. The thermosensitive nanosensor of claim 1, wherein the thermosensitive hydrogel surrounds the plurality of the conductive coated nanostructures.

9. The thermosensitive nanosensor of claim 1, wherein the thermosensitive hydrogel and cover layer form a covered thermosensitive hydrogel ring which surrounds the plurality of the conductive coated nanostructures.

10. The thermosensitive nanosensor of claim 9, wherein the covered thermosensitive hydrogel ring surrounds the substrate.

11. The thermosensitive nanosensor of claim 1, wherein the nanostructures are made of a polymer.

12. The thermosensitive nanosensor of claim 11, wherein the polymer is embedded into a matrix polymer to form a yarn.

13. The thermosensitive nanosensor of claim 12, wherein the yarn is a micro denier yarn.

14. The thermosensitive nanosensor of claim 12, wherein the matrix polymer is made of a material selected from the group consisting of polystyrene, polyvinyl alcohol, ethylene vinyl alcohol, polyacrylamide and poly lactic acid.

15. The thermosensitive nanosensor of claim 12, wherein the matrix polymer is made of a polyethylene terephthalate modified with sulfonated isocyanate.

16. The thermosensitive nanosensor of claim 2, wherein the conductive material comprises at least one of metals, alloys, and graphene structures.

17. The conductive layer of claim 1, wherein the conductive material comprises at least one of metals, alloys, and graphene structures.

18. The thermosensitive nanosensor of claim 1, wherein the thermosensitive hydrogel is applied as a protective conformal coating film.

19. The thermosensitive nanosensor of claim 1, wherein the nanostructures are made of a polymer material selected from the group of polyesters consisting of polyethylene terephthalate, polyethylene naphthanate or polybutylene terephthalate.

20. The thermosensitive nanosensor of claim 1, wherein the nanostructures are made of a polyester and/or polyether-based polyurethane.

21. The thermosensitive nanosensor of claim 1, wherein the nanostructures are made of polyolefins such as polypropylene.

22. The thermosensitive nanosensor of claim 1, wherein the thermosensitive hydrogel layer is applied as an annular ring.

23. A 3-electrode chemical cell, comprising an array of thermosensitive nanosensors according to claim 1 internconnected to provide a working electrode, a reference electrode and a counter electrode.

24. The thermosensitive nanosensor of claim 1, wherein an enzyme or buffer is included in the hydrogel, the enzyme or buffer selected to detect a metabolite.

25. The thermosensitive nanosensor of claim 1, wherein the hydrogel comprises a comb-like structure formed by grafting polymer chains with hydrophilic end groups such as amines, amides, acrylates.

26. The thermosensitive nanosensor of claim 1, wherein the hydrogel is a hydrogel polymer network comprising hydrophilic groups selected from the group consisting of amines, amides, and acrylates.

27. The thermosensitive nanosensor of claim 1, wherein the hydrogel is an interpenetrating polymer network gel.

28. The thermosensitive nanosensor of claim 26, wherein the interpenetrating polymer network gel includes polyacrylamide and polyacrylate.

29. The thermosensitive nanosensor of claim 1, wherein the hydrogel is selectively crosslinked by varying the concentration of initiator used during hydrogel polymerization.

30. The thermosensitive nanosensor of claim 1, wherein the thermosensitive hydrogel has a micelle like structure which opens up on contact with moisture.

31. The thermosensitive nanosensor of claim 1, wherein the cover layer is in the form of elastomers, fibers or films from at least one of the natural, synthetic, and inorganic polymers.

* * * * *